United States Patent [19]
Pawluskiewicz

[11] Patent Number: 6,007,490
[45] Date of Patent: Dec. 28, 1999

[54] ULTRASONIC PROBE WITH DISCONNECTABLE TRANSDUCER

[75] Inventor: Peter M. Pawluskiewicz, Seattle, Wash.

[73] Assignee: ATL Ultrasound, Inc., Bothell, Wash.

[21] Appl. No.: 09/200,347

[22] Filed: Nov. 25, 1998

[51] Int. Cl.[6] ................................................ A61B 8/00
[52] U.S. Cl. ................................................ 600/459
[58] Field of Search ........................... 439/909; 600/437, 600/438, 459, 451

[56] References Cited

U.S. PATENT DOCUMENTS

| | | | |
|---|---|---|---|
| 5,083,568 | 1/1992 | Shimazaki et al. | 600/459 |
| 5,160,269 | 11/1992 | Fox, Jr. et al. | |
| 5,163,436 | 11/1992 | Saitoh et al. | 600/459 |
| 5,167,231 | 12/1992 | Matsui | 600/459 |

Primary Examiner—Jeffrey R. Jastrzab
Assistant Examiner—Maulin Patel
Attorney, Agent, or Firm—W. Brinton Yorks, Jr.

[57] ABSTRACT

An ultrasonic transducer probe that provides a connector for quickly, easily, and reliably connecting and disconnecting the transducer electrical connections in such a manner that the connection is removable. In a preferred embodiment of the present invention, the connector provides means for receiving one end of a flex circuit that is attached at its other end to a multi-element transducer located at the distal end of a probe. The flex circuit is oriented and aligned in the connector with a separate flex circuit in such a manner that compression of the connector sections creates an electrical connection between the flex circuits. Since the connector is solderless, the flex circuits may be removed and replaced without damage to the flex circuits or flex circuit conductors.

19 Claims, 8 Drawing Sheets

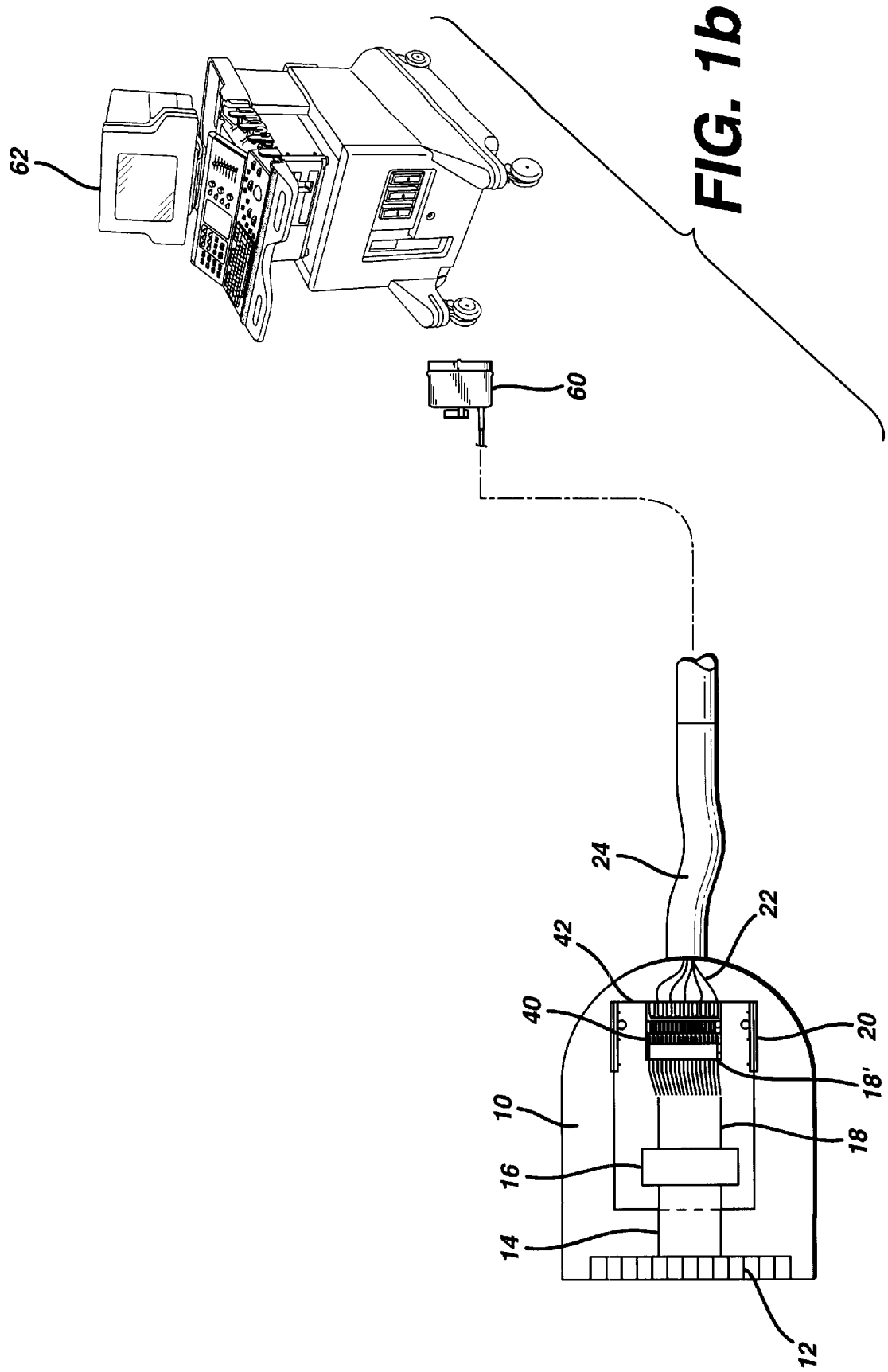

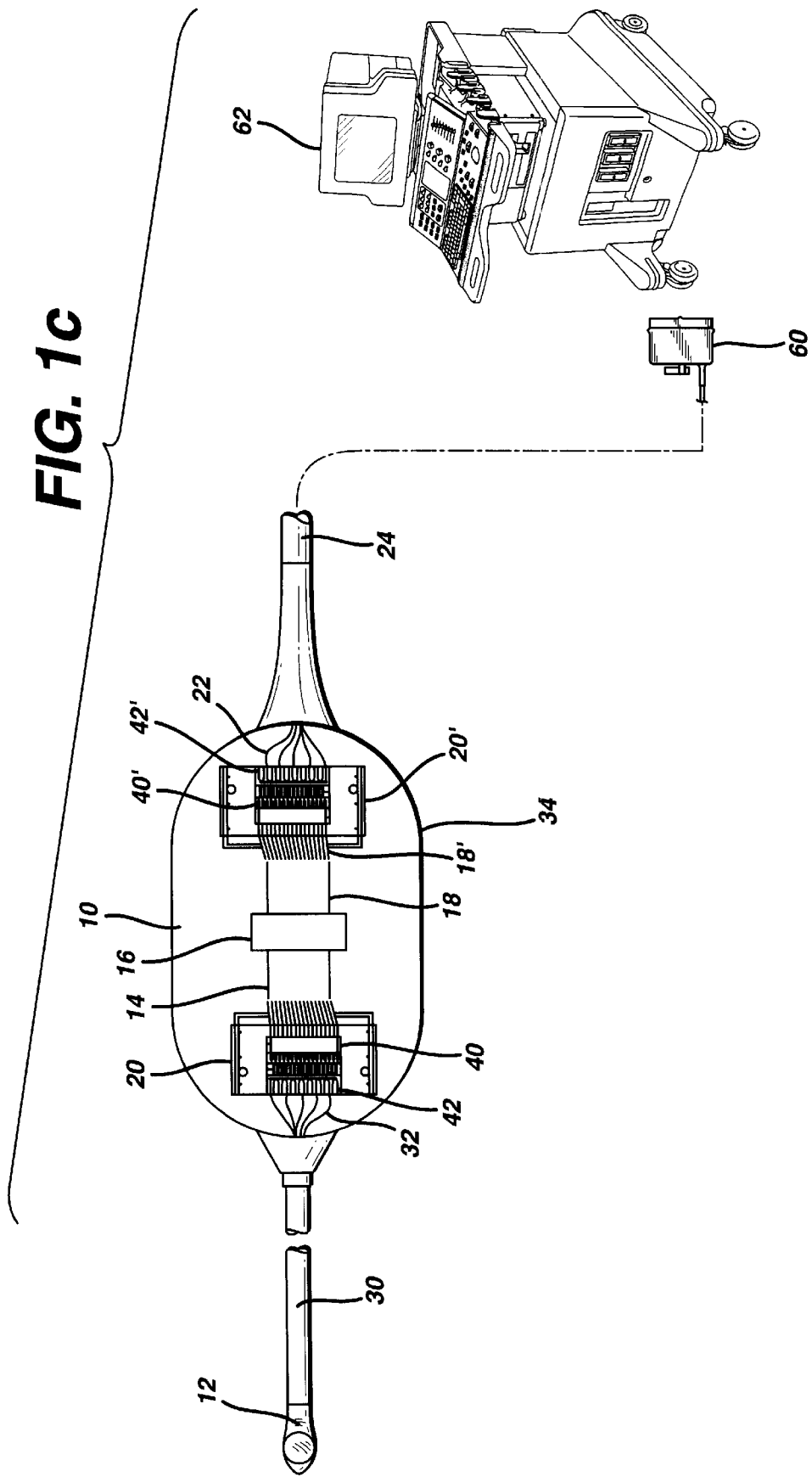

ULTRASONIC PROBE WITH DISCONNECTABLE TRANSDUCER

This invention relates to ultrasonic transducer probes utilized by ultrasonic diagnostic imaging systems to provide diagnostic information concerning a medical patient and, in particular, to probes that have internal connectors for quickly, easily, and reliably connecting and disconnecting the ultrasonic transducer within the probe.

Ultrasonic diagnostic imaging systems are in widespread use for performing ultrasonic imaging and measurements through the use of probes which may be placed internal or external to the body being measured. Such probes include transducers for transmitting pulses of energy into the body, and for receiving the returning pulses of energy as they are reflected from internal structures of the body.

The transducer is a piezoelectric element that is generally made of a crystalline material such as barium titanate. The individual elements of a multi-element or array transducer are generally rectangular in shape and are very small. The widths of the individual transducer elements range down to only a few thousandths of an inch. A multi-element or array transducer has a multitude of elements, and can range from 64 to in excess of 380 individual elements. Each transducer element has a separate signal electrode for transmitting and receiving electrical signals through a scan head cable, which is coupled to the ultrasonic diagnostic imaging system. With the small size and considerable number of elements in a multi-element or array transducer, means must be provided for accurately and reliably making the necessary electrical connections between the individual transducer elements and the scan head cable leading to the ultrasound system.

High frequency ultrasonic transducer arrays are intended to receive the pulses of energy, or echos, of the lowest intensity possible at very high frequencies. Accordingly, it is imperative that all of the electrical connections made to the transducer are reliable and that the electrical characteristics of the transducer elements be refined to as great of degree as possible. It is essential that no spurious or harmful electrical conditions be introduced or engendered such as ground current conditions. For example, such conditions could arise if sections of a conductor, which are to be maintained at ground reference potential, are not positively and uniformly maintained at that potential.

It is well known that the transducer signal electrodes may be coupled to the ultrasonic diagnostic imaging system by a substrate such as a flex circuit as shown in U.S. Pat. No. 5,275,167. A flex circuit is shown in the preferred embodiments of the present invention, however, those skilled in the art will readily appreciate the use of other substrates that have a plurality of electrical conductors for transducer connections or a single electrical conductor for grounding circuits. Such substrates may have varying degrees of flexibility, rigidity and thickness and may even consist of a printed circuit board or plurality of individual conductors held in a predetermined pattern by adhesive or compressive means.

After the individual conductors of the flex circuit are connected to the transducer signals, the other end of the individual conductors are typically soldered to electrical conductors on a printed circuit board or to coaxial wires as shown in U.S. Pat. No. 5,381,795. The other end of such a printed circuit board or coaxial cable is then coupled to the ultrasonic diagnostic imaging system. The soldering of the flex circuit conductors to a printed circuit board or coaxial wires is difficult because of the small size of the flex circuit conductors, the small size of the coaxial wires, and the large number of individual connections. Those soldered connections must be uniform and reliable such that the characteristics of the electrical connection do not cause harm to or introduce erroneous electrical signals into the transducer signal that is carried on the electrical conductor.

The method of individually soldering each flex circuit conductor, which represents an electrical connection to an individual transducer element, increases the risk of a malfunctioning transducer and thus increases the possible need for repair. The repair of the transducer is even more cumbersome and difficult because each solder connection on the flex circuit must be un-soldered, the flex circuit must then be removed, replaced, and each solder connection on the flex circuit must be re-soldered. Accordingly, each time a transducer is replaced or repaired, the risk of further damage or transducer malfunction is increased. Moreover, the process of un-soldering and soldering each flex circuit conductor is time consuming and is difficult due to the intense concentration required by the worker making the individual solder connections.

It would be preferable to be able to connect and disconnect all of the individual transducer elements at one time in a quick, easy, and reliable manner. Such a connection and disconnection of the transducer elements will significantly increase the reliability and consistency of the individual transducer element connections to the ultrasonic diagnostic imaging system. Moreover, such a quick and easy connection will reduce the time of installation and repair, and reduce the stress level on the workers making the individual solder connections.

In accordance with the principles of the present invention, a probe is provided with a connector for quickly, easily, and reliably connecting and disconnecting all of the electrical conductors between the transducer electrode signals and the ultrasonic diagnostic imaging system at one time. Since the connector of the present invention provides a removable connection without the use of solder, the flex circuits may be removed from the connector without damage to the flex circuits or flex circuits' conductors and reused.

In the drawings:

FIGS. 1a, 1b, and 1c illustrate an ultrasonic probe constructed in accordance with the principles of the present invention;

Figure 1A:
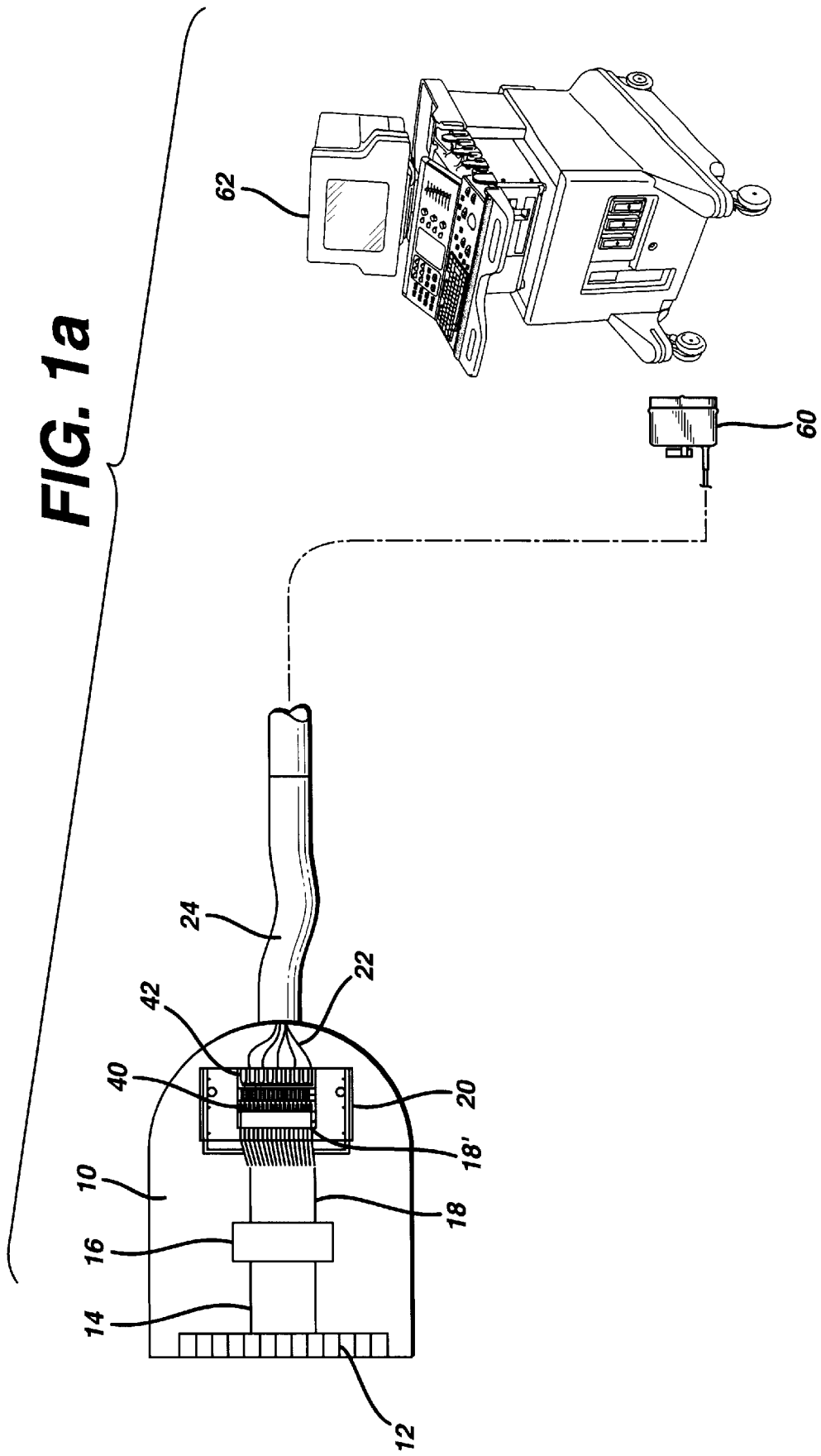

Referring first to FIGS. 1a and 1b, an ultrasonic probe constructed in accordance with the principles of the present invention for use external the body being measured is shown. The probe 10 is shown connected to ultrasonic diagnostic imaging system 62 by coaxial cable 24, which has coaxial conductors 22. The probe 10 has an ultrasonic transducer 12, flex circuits 14 and 18, connector 16, and printed circuit board 20 having electrical tabs 40 and 42.

To electrically couple transducer 12 to ultrasonic diagnostic imaging system 62, one end of flex circuit 14 is electrically connected to transducer 12 as described in greater detail below and in FIGS. 2a and 2b. The other end of flex circuit 14 is then electrically connected to flex circuit 18 by connector 16. The electrical conductors 18' of flex circuit 18 are connected to the printed circuit board 20 by electrical tabs 40. Tabs 40 are electrically connected to tabs 42 and may be routed through electronic components (not shown) on printed circuit board 20 if desired. Tabs 42 are then electrically connected to coaxial conductors 22 of cable 24 as described in U.S. Pat. No. 5,482,047. To complete the electrical connection from transducer 12 to ultrasonic diagnostic imaging system 62, coaxial conductors 22 are connected at the other end of cable 24 to connector 60. As shown in FIG. 1a, connector 16 may be unmounted and move freely within the probe, or as shown in FIG. 1b, connector 16 may be securely fastened to a printed circuit board 20.

Referring now to FIG. 1c, an ultrasonic probe constructed in accordance with the principles of the present invention for insertion into the body cavity is shown. The probe 10 is shown connected to ultrasonic diagnostic imaging system 62 by coaxial cable 24 having coaxial conductors 22. In a preferred embodiment, the probe 10 has an ultrasonic transducer 12, an endoscope tube section 30, coaxial conductors 32, and a housing 34 that may house electrical and mechanical controls for controlling the movement of the transducer and endoscope. The housing may also house printed circuit board 20 which has electrical tabs 40 and 42 and printed circuit board 20' which has electrical tabs 40' and 42'.

Figure 2A:
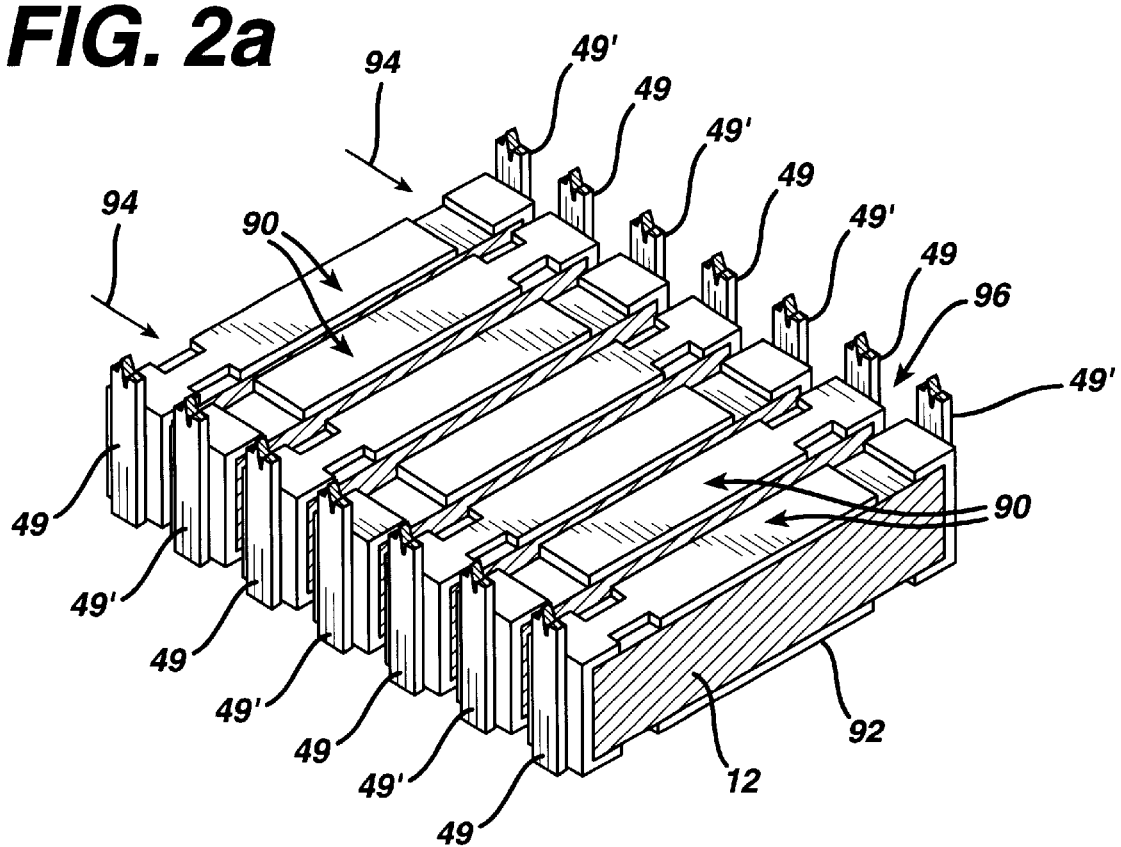
FIGS. 2a and 2b illustrate the construction of an ultrasonic array transducer.
Figure 2B:
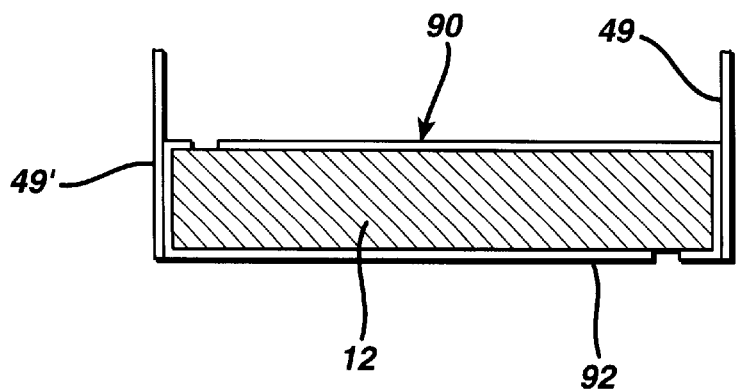

Coaxial conductors 32 are connected to transducer 12 as described in greater detail below, and as shown in FIGS. 2a and 2b. Coaxial conductors 32 extend through endoscopic tube section 30 and are electrically connected to tabs 40 on printed circuit board 20. Coaxial conductors 32 are then electrically extended to flex circuit 14 through tabs 42 and electronic components (not shown) on printed circuit board 20 if desired. Flex circuit 14 is then electrically connected at its other end to flex circuit 18 by connector 16. Flex circuit 18 is then coupled to ultrasonic diagnostic imaging system 62 through printed circuit board 20' in the same manner as shown in FIGS. 1a and 1b.

Similar to the configurations shown in FIGS. 1a and 1b, connector 16 may be unmounted and move freely within housing 34 or connector 16 may be securely fastened (not shown) to printed circuit board 20 or 20'. FIG. 1c shows connector 16 located between printed circuit boards 20 and 20' rather than between the transducer and the printed circuit board 20 as shown in FIGS. 1a and 1b. It will be appreciated to those skilled in the art that flex circuits 14 and 18, circuit board 20 or 20', and connector 16 may be arranged in a variety of configurations in accordance with the principles of the present invention.

Turning now to FIGS. 2a and 2b, enlarged views of transducer 12 are shown. A plate of piezoelectric ceramic 12 is initially covered on its two planar surfaces and edges with a metallized electrode coating. Laser cutting or photolithography is then used to form holes in the electrode coating in the longitudinal directions indicated by arrows 94. The ceramic plate and its metallized coating are then diced into individual transducer elements and electrodes by transverse dicing as indicated by arrow 96. The result is a series of transducer elements and electrodes as shown in FIGS. 2a and 2b. Signal electrodes 90 are located on one planar surface of the transducer 12 and wrap around one end of the transducer elements. Return electrodes 92 are located on the other planar surface of the transducer and wrap around the other end of the transducer elements as shown in FIG. 2a.

The laser formed cuts and notches result in an alteration of the signal and return ends of the transducer elements from one element to another. That is, conductors 49 are connected to signal electrodes 90, and interspaced conductors 49' are connected to return electrodes 92. Conductors 49 extend from transducer electrodes 90 and are joined to individual conductors of flex circuit 14. Conductors 49' extend from transducer electrodes 92 and are typically joined together and routed back to the ultrasonic diagnostic imaging system 62 through the shielding on individual coaxial cables or on a single conductor.

Figure 3A:
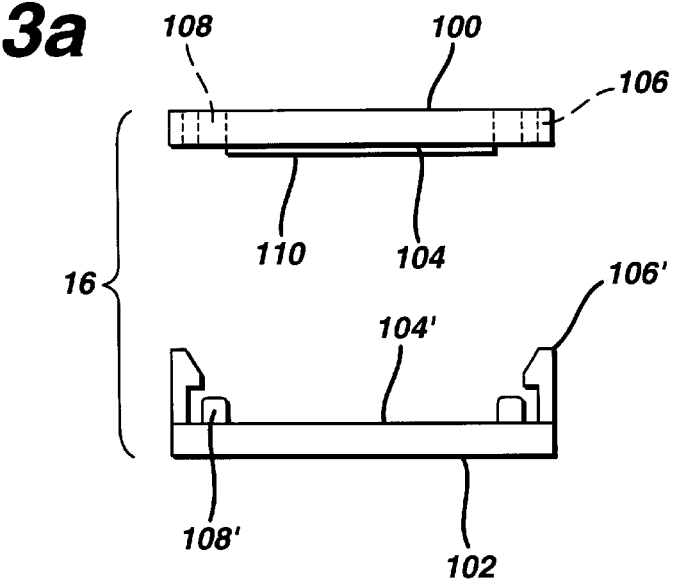
FIGS. 3a, 3b, 3c and 3d illustrate a connector constructed in accordance with the principles of the present invention.

Turning now to FIGS. 3a–3d, connector 16 and its connection of flex circuits 14 and 18 are shown. FIG. 3a shows connector 16, which includes cover section 100 and receiving section 102, where the cover and receiving sections each have solderless mating surfaces 104 and 104' respectively. Cover section 100 has fastening notches 106 and alignment notches 108 while receiving section 102 has fastening pins 106' and alignment guides 108'. Cover section 100 is shown with elastomer 110 attached to solderless mating surface 104.

Figure 3B:
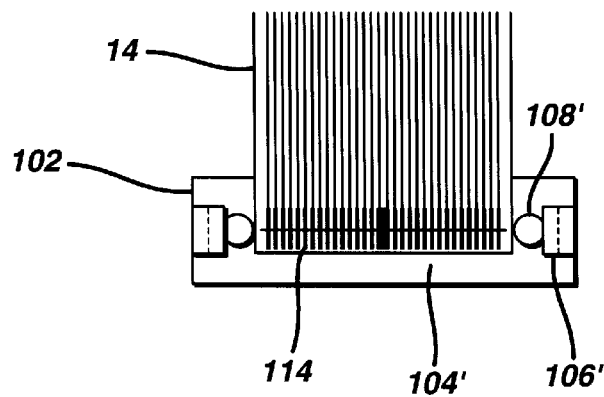

FIG. 3b shows a top view of receiving section 102 with flex circuit 14. Flex circuit 14 is shown with exposed conductors 114 and is located on solderless mating surface 104' between alignment guides 108'. Flex circuit 14 is oriented in the receiving section such that exposed conductors 114 are in a position to be aligned with and electrically connected to exposed electrical conductors of a separate flex circuit.

Figure 3C:
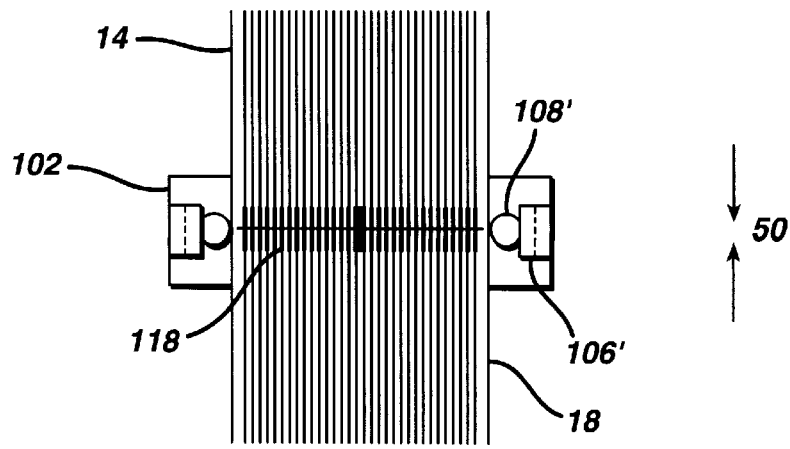

FIG. 3c shows flex circuits 14 and 18 oppposingly oriented and aligned in receiving section 102 in an overlapping fashion between alignment guides 108' such that exposed conductors 114 and 118 are aligned with and in a position to be electrically connected to each other once compressed. The spatial alignment of exposed conductors 114 and 118 is precisely matched to assure that reliable and quality electrical connections are made when flex circuits 14 and 18 are oppposingly oriented, aligned, and compressed between the receiving section 102 and the cover section 100. FIG. 3c shows flex circuits 14 and 18 engaging the receiving section 102 from different directions as indicated by arrows 50. If desired, flex circuits 14 and 18 may engage receiving section 102 from the same direction such that flex circuit 14 and flex circuit 18 are substantially overlapping (not shown).

Figure 3D:
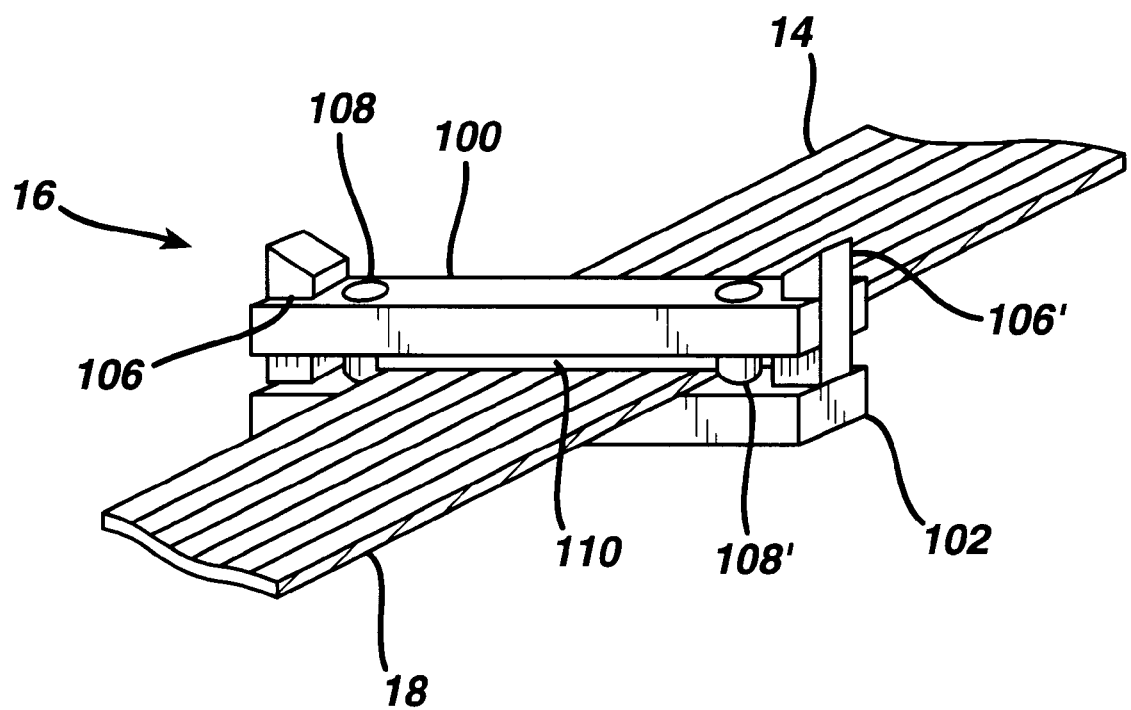

Once flex circuits 14 and 18 are properly aligned and oriented in receiving section 102, the fastening notches 106 and alignment notches 108 are positioned over fastening pins 106' and alignment guides 108', respectively. Once positioned, a downward pressure is applied to cover section 100 until the cover section and receiving section 102 are securely fastened by fastening notches 106 and fastening pins 106'. Flex circuits 14 and 18 are now compressed and securely held in place between the solderless mating surfaces 104 and 104' such that exposed conductors 114 and 118 are electrically connected. Elastomer 110 provides a consistent and snug compression of the flex circuits. FIG. 3d shows connector 16 with flex circuits 14 and 18 properly oriented and aligned in relation to each other, and compressed and fastened between cover section 100 and receiving section 102.

The orientation, alignment, compression, and fastening of flex circuits 14 and 18 create a solderless and removable electrical connection between the individual signal electrodes 90 and the ultrasonic diagnostic imaging system 62. Once the transducer signal electrodes 90 have been coupled to ultrasonic diagnostic imaging system 62 through connector 16, the transducer may now be reliably removed and replaced by removing cover section 100 from receiving section 102. Once the cover section is removed, flex circuits 14 and 18 can be quickly and easily removed. Connector 16 provides a significant improvement over connectors that require solder to secure an electrical connection between separate conductors due to the solderless mating surfaces 104 and 104', which permit the same flex circuit to be connected and disconnected without damage to the flex circuit or the flex circuits' conductors.

Figure 4A:
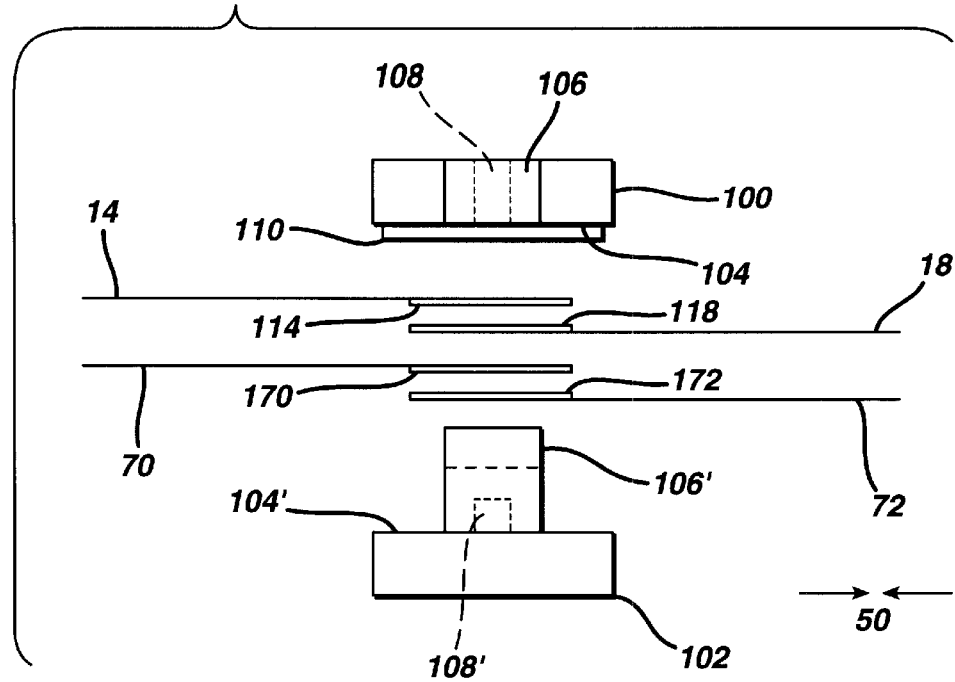
FIGS. 4a and 4b illustrate other embodiments of the present invention where the connector of FIG. 3a is used to connect a plurality of flex circuits.
Figure 4B:
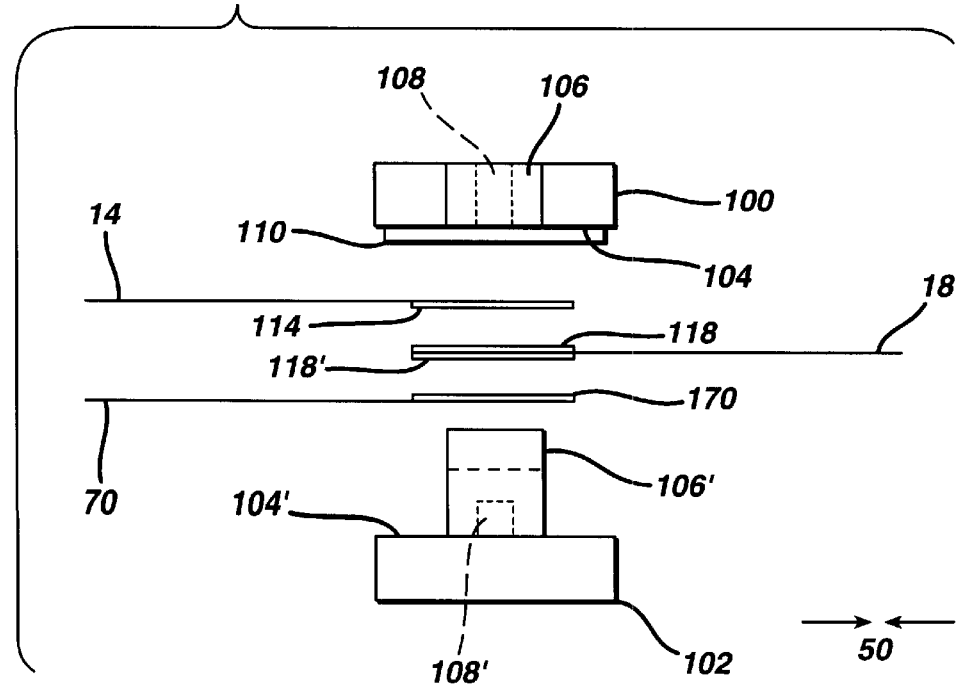

Turning now to FIGS. 4a and 4b, embodiments of the present invention are shown where a plurality of flex circuits are compressed in connector 16 in the same manner shown in FIG. 3d. FIG. 4a shows connector 16, flex circuit 14 with exposed conductors 114, flex circuit 18 with exposed conductors 118, flex circuit 70 with exposed conductors 170, and flex circuit 72 with exposed conductors 172. Flex circuits 14 and 18 are aligned with each other in the same manner as shown in FIGS. 3b–3d. Flex circuit 70 is shown oriented and aligned with flex circuit 72 in such a manner that exposed conductors 170 are opposingly oriented and aligned with exposed conductors 172. Flex circuits 14 and 18 are oriented and aligned in relation to flex circuits 70 and 72 such that exposed conductors 114 and 118 are electrically independent and insulated from electrical conductors 170 and 172.

FIG. 4b shows yet another embodiment of the present invention where flex circuit 14 is shown with exposed conductors 114 and flex circuit 18 is shown with exposed conductors 118 on one of its sides and exposed conductors 118' on its other side. Exposed conductors 118 and 118' are shown as being electrically independent of each other; however, if desired, exposed conductors 118 and 118' may be electrically coupled. Flex circuit 70 is shown with exposed conductors 170 on only one side of the flex circuit. If desired, flex circuits 14 and 70 may have exposed conductors on each side of the flex circuit as shown for flex circuit 18.

Flex circuits 14 and 18 are aligned between alignment guides 108' in the same manner shown in FIGS. 3c and 3d. Flex circuit 70 is shown oriented in such a manner that exposed conductors 170 are facing and aligned with exposed conductors 118'. When cover section 100 and receiving section 102 are compressed as shown in FIG. 3d, exposed conductors 114 will be electrically connected to exposed conductors 118 and exposed conductors 170 will be electrically connected to exposed conductors 118'.

It will be appreciated that numerous configurations of the embodiments described in FIGS. 4a and 4b may be readily obtained by those skilled in the art. For example, a plurality of flex circuits may be added to the configurations shown in FIGS. 4a and 4b by appropriately sizing connector 16. Also, FIGS. 4a and 4b show flex circuits 14 and 18, and flex circuits 70 and 72 positioned in the receiving section 102 in different directions as indicated by arrows 50. If desired, flex circuits 14 and 18, and/or 70 and 72, may be positioned in receiving section 102 from the same direction such that some or all of the flex circuits are substantially overlapping.

Figure 5:
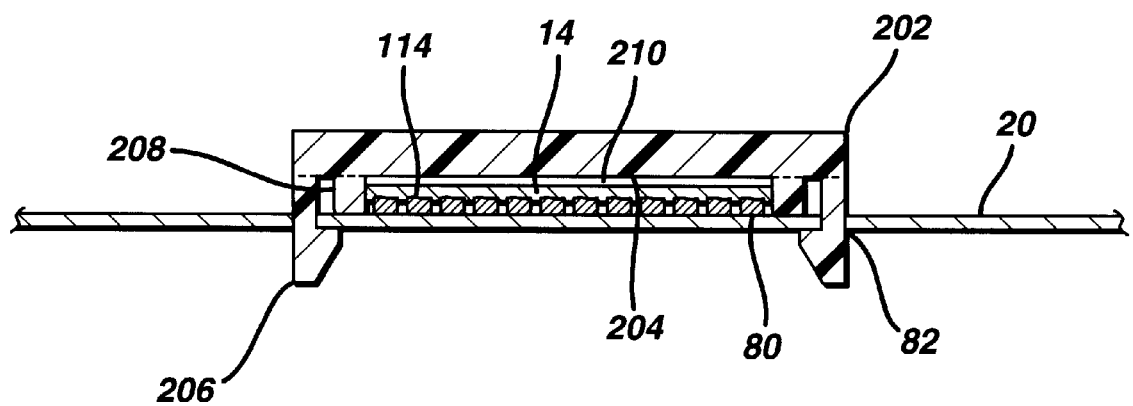
FIG. 5 illustrates another embodiment of the present invention where a portion of the connector of FIG. 3a is affixed to a printed circuit board.

FIG. 5 shows yet another embodiment of the present invention where receiving section 202 is shown connecting flex circuit 14 to printed circuit board 20. Printed circuit board 20 provides exposed conductors 80 and machined fastening holes 82. Receiving section 202 provides fastening pins 206, alignment guides 208, solderless mating surface 204, and an optional elastomer like material 210. Receiving section 202 differs from receiving section 102 in that receiving section 202 has elastomer 210 affixed to solderless mating surface 204.

Flex circuit 14 is connected at one end to transducer 12 or to another printed circuit board as shown in FIG. 1c. The other end of flex circuit 14 having exposed conductors 114, is connected to printed circuit board 20. Similar to the methods described above, flex circuit 14 is placed on the solderless mating surface 204 and elastomer 210, between alignment guides 208. Flex circuit 14 is shown opposingly oriented and aligned in the receiving section such that exposed conductors 114 are aligned with and opposing conductors 80. The spatial alignment of exposed conductors 114 and 80 are precisely matched to assure that reliable and quality electrical connections are made when flex circuit 14 is aligned and compressed between receiving section 202 and printed circuit board 20.

Once flex circuit 14 is properly oriented and aligned, and fastening pins 206 are positioned over machined fastening holes 82, a downward pressure is applied to receiving section 202 such that flex circuit 14 is compressed and held in place between solderless mating surface 204, elastomer 210, and the printed circuit board 20. When the receiving section and flex circuit are compressed and securely attached to the printed circuit board, exposed conductors 114 will be electrically connected to exposed conductors 80. It will be appreciated by those skilled in the art that a plurality of flex circuits may be added to the embodiment shown in FIG. 5 in the same manner as described in FIGS. 4a–4b.

In all of the embodiments of the present invention, the conductors of the flex circuits are preferably tinned in gold or an indium based tinning agent such that the compression of the flex circuits creates a superior electrical connection between the flex circuit conductors.

What is claimed is:

1. A connector for removably connecting a plurality of substrates, wherein each substrate has one or more electrical conductors spatially arranged thereon in a predetermined pattern, comprising:

a receiving section having a solderless mating surface for receiving and holding said substrates;

alignment means for aligning said substrates in said receiving section, wherein said conductors are aligned for electrical connection;

a cover section having a solderless mating surface for removably compressing and electrically connecting said substrates between said receiving section and said cover section; and fastening means for removably fastening and connecting said cover section to said receiving section.

2. The connector of claim 1, wherein said cover section solderless mating surface further includes fitting means for snugly fitting said substrates between said cover section and said receiving section.

3. The connector of claim 1 or 2, wherein said alignment means include alignment guides spatially aligned with and protruding outwardly from said receiving section solderless mating surface.

4. The connector of claim 3, wherein said alignment means further include alignment notches spatially aligned and opposing said alignment guides, deposited within said cover section solderless mating surface.

5. A connector for removably connecting a plurality of substrates, wherein each substrate has one or more electrical conductors spatially arranged thereon in a predetermined pattern, comprising:

a receiving section having a solderless mating surface for receiving and compressing said substrates between said receiving section and one of said substrates;

alignment means for aligning said substrates in said receiving section, wherein said conductors are aligned for electrical connection; and fastening means for removably fastening and connecting said receiving section to one of said substrates.

6. The connector of claim 5, wherein said solderless mating surface further includes fitting means for snugly fitting said substrates between said receiving section and said one substrate.

7. The connector of claim 5 or 6, wherein said alignment means include alignment guides spatially aligned on and protruding outwardly from said solderless mating surface.

8. The connector of claim 5 or 6, wherein said fastening means protrude outwardly from said receiving section and securely fasten said receiving section to said one substrate.

9. An ultrasonic transducer probe having an array transducer located at a distal end thereof for ultrasonic scanning, and a cable which may be coupled to an ultrasonic diagnostic imaging system, comprising:
   a receiving section having a solderless mating surface for receiving and holding a plurality of substrates having a one or more electrical conductors spatially arranged thereon, wherein a first substrate is coupled to said array transducer and a second substrate is coupled to said cable;
   alignment means for aligning said substrates in said receiving section, wherein said conductors are aligned for electrical connection;
   a cover section having a solderless mating surface for removably compressing said substrates and electrically connecting said conductors between said receiving section and said cover section; and
   fastening means for removably fastening and connecting said cover section to said receiving section.

10. The probe of claim 9, wherein said cover section solderless mating surface further includes fitting means for snugly fitting said substrates between said cover section and said receiving section.

11. The probe of claim 9 or 10, wherein said alignment means include alignment guides spatially aligned with and protruding outwardly from said receiving section solderless mating surface.

12. The probe of claim 11, wherein said alignment means further include alignment notches spatially aligned and opposing said alignment guides on said cover section solderless mating surface.

13. An ultrasonic transducer probe having a transducer located at a distal end thereof for ultrasonic scanning, coupled to an ultrasonic diagnostic imaging system, comprising:
   a receiving section having a solderless mating surface for receiving and holding a plurality of substrates, wherein each substrate has one or more electrical conductors spatially arranged thereon,
   wherein said receiving section further provides means for removably compressing said substrates between said receiving section and one of said substrates;
   alignment means for aligning said substrates in said receiving section, wherein said conductors are aligned for electrical connection; and
   fastening means for removably fastening and connecting said receiving section to one of said substrates.

14. The probe of claim 13, wherein said solderless mating surface further includes fitting means for snugly fitting said substrates between said receiving section and one of said substrates.

15. The probe of claim 13 or 14, wherein said alignment means include alignment guides spatially aligned and protruding transversely from said solderless mating surface.

16. An ultrasonic transducer probe having an array transducer located at a distal end thereof for ultrasonic scanning, coupled to an ultrasonic diagnostic imaging system, comprising:
   a receiving section for receiving and holding a plurality of substrates, wherein each substrate has one or more electrical conductors spatially arranged thereon in a predetermined pattern,
   wherein one of said substrates is electrically connected at one end to said array transducer and the other end is received in said receiving section,
   wherein another of said substrates is electrically coupled to said system at one end and the other end is received in said receiving section;
   alignment means for aligning said substrates in said receiving section, wherein said conductors are aligned for electrical connection;
   a cover section for removably compressing said substrates and electrically connecting said conductors between said receiving section and said cover section; and
   fastening means for removably fastening and connecting said cover section to said receiving section.

17. The connector of claim 16, wherein said cover section further includes fitting means for snugly fitting said substrates between said cover section and said receiving section.

18. An ultrasonic transducer probe having a multi-element transducer located at a distal end thereof for ultrasonic scanning, coupled to an ultrasonic diagnostic imaging system, comprising:
   a receiving section for receiving and compressing a plurality of substrates between said receiving section and one of said substrates,
   wherein each substrate has one or more electrical conductors spatially arranged thereon in a predetermined pattern,
   wherein one of said substrates is electrically connected at one end to said multi-element transducer and the other end of said one substrate is received in said receiving section,
   wherein another of said substrates is electrically coupled to said system at one end and the other end is received in said receiving section;
   alignment means for aligning said substrates in said receiving section, wherein said conductors are aligned for electrical connection;
   fastening means for removably fastening and connecting said receiving section to one of said substrates.

19. The connector of claim 18, wherein said receiving section further includes fitting means for snugly fitting said substrates between said cover section and said receiving section.

* * * * *